US008349817B2

(12) United States Patent
Persichetti et al.

(10) Patent No.: US 8,349,817 B2
(45) Date of Patent: *Jan. 8, 2013

(54) ANALOGUES OF CILOSTAZOL

(75) Inventors: Rose A. Persichetti, Stow, MA (US);
Julie F. Liu, Lexington, MA (US); Craig E. Masse, Cambridge, MA (US); Scott L. Harbeson, Cambridge, MA (US)

(73) Assignee: CoNCERT Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/644,758

(22) Filed: Dec. 22, 2009

(65) Prior Publication Data

US 2010/0249079 A1     Sep. 30, 2010

Related U.S. Application Data

(63) Continuation-in-part of application No. 12/150,107, filed on Apr. 24, 2008, now abandoned.

(60) Provisional application No. 61/203,577, filed on Dec. 23, 2008, provisional application No. 60/926,100, filed on Apr. 25, 2007.

(51) Int. Cl.
| A61K 31/4709 | (2006.01) |
| A61K 31/4365 | (2006.01) |
| A61K 31/616 | (2006.01) |
| A61P 3/10 | (2006.01) |
| A61P 9/00 | (2006.01) |
| A61P 9/10 | (2006.01) |
| A61P 11/06 | (2006.01) |
| A61P 29/00 | (2006.01) |
| C07D 401/12 | (2006.01) |

(52) U.S. Cl. ......... 514/161; 514/301; 514/312; 546/158
(58) Field of Classification Search ........................ None
See application file for complete search history.

(56) References Cited

U.S. PATENT DOCUMENTS

| 4,277,479 A * | 7/1981 | Nishi et al. .................... 514/312 |
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 2007/0082929 A1 | 4/2007 | Gant et al. |
| 2007/0197695 A1 | 8/2007 | Potyen et al. |
| 2008/0103122 A1 | 5/2008 | Veltri |
| 2009/0042842 A1 | 2/2009 | Liu et al. |

FOREIGN PATENT DOCUMENTS

| WO | WO 95/26325 | 10/1995 |
| WO | WO 2007/118651 | 10/2007 |
| WO | WO 2007/118651 A1 | 10/2007 |
| WO | WO 2008/133949 A1 | 11/2008 |

OTHER PUBLICATIONS

Mallikaarjun et al., Interaction Potential and Tolerability of the Coadministration of Cilostazol and Aspirin, 37 (Suppl. 2) Clin. Pharmacokinet 87-93 (1999).*

Food Drug Administration's, Guidance for Industry, Sterile Drug Products Produced by Aseptic Processing—Current Good Manufacturing Practice (Sep. 2004).*
PCT International Search Report for International Application No. PCT/US2008/005301, Date of Mailing: Aug. 26, 2008.
PCT Written Opinion of the International Searching Authority for International Application No. PCT/US2008/005301, Date of Mailing: Aug. 26, 2008.
Fisher, M.B. et al., "The Complexities Inherent in Attempts to Decrease Drug Clearance by Blocking Sites of CYP-Mediated Metabolism," *Curr. Opin. Drug Discov.*, 9(1): 101-109 (Jan. 2006).
Kushner, D.J. et al., "Pharmacological Uses and Perspectives of Heavy Water and Deuterated Compounds," *Can. J. Physiol. Pharmacol.*, 77(2): 79-88 (Feb. 1999).
Physicians' Desk Reference® product label and information for PLETAL®, *Physicians' Desk Reference*, Edition 63, 2009, pp. 2481-2484 (month not available).
Baillie, Thomas A., "The Use of Stable Isotopes in Pharmacological Research", *Pharmacological Reviews*, vol. 33, No. 2, pp. 81-132, 1981.
Browne, Thomas R., "Stable Isotope Techniques in Early Drug Development: An Economic Evaluation", *J. Clin. Pharmacol*, vol. 38, pp. 213-220, 1998.
Cherrah, et al., "Study of Deuterium Isotope Effects on Protein Binding by Gas Chromatography/Mass Spectrometry. Caffeine and Deuterated Isotopomers", *Biomedical and Environmental Mass Spectrometry*, vol. 14, pp. 653-657, 1987.
Dyck, et al., "Effects of Deuterium Substitution on the Catabolism of β-Phenylethylamine: An In Vivo Study", *Journal of Neurochemistry*, vol. 46, No. 2, pp. 399-404, 1986.
Fisher, et al., "The complexities inherent in attempts to decrease drug clearance by blocking sites of CYP-mediated metabolism", *Current Opinion in Drug Discovery Development*, vol. 9, No. 1, pp. 101-109, 2006.
Foster, Allan B., "Deuterium isotope effects in studies of drug metabolism", *TIPS*, pp. 524-527, Dec. 1984.
Foster, Allan B., "Deuterium isotope effects in the metabolism of drugs and xenobiotics", *Advances in Drug Research* vol. 14, pp. 2-40, 1985.
Gouyette, et al., "Synthesis of Deuterium-labelled Elliptinium and its Use in Metabolic Studies", *Biomedical and Environmental Mass Spectrometry*, vol. 15, pp. 243-247, 1988.
Haskins, N.J., "The Application of Stable Isotopes in Biomedical Research", *Biomedical Mass Spectrometry*, vol. 9, No. 7, pp. 269-277, 1982.

(Continued)

*Primary Examiner* — Janet Andres
*Assistant Examiner* — Timothy R Rozof
(74) *Attorney, Agent, or Firm* — Kenyon & Kenyon LLP

(57) ABSTRACT

This invention relates to novel compounds which are derivatives of the phosphodiesterase inhibitor, cilostazol and pharmaceutically acceptable salts thereof. This invention also provides pyrogen-free compositions comprising one or more compounds of the invention and the use of the disclosed compounds and compositions in methods of treating diseases and conditions that are treated by administration of a phosphodiesterase inhibitor, such as cilostazol. The invention also relates to the use of the disclosed compounds and compositions as reagents in analytical studies involving cilostazol.

8 Claims, No Drawings

OTHER PUBLICATIONS

Honma, et al., "Liberation of Deuterium from the Piperidine Ring during Hydroxylation", *Drug Metabolism and Disposition*, vol. 15, No. 4, pp. 551-559, 1987.

Kushner, et al., "Pharmacological uses and perspectives of heavy water and deuterated compounds", *Can J Physiol. Pharmacol.*, vol. 77, pp. 79-88, 1999.

Pieniaszek, et al., "Moricizine Bioavailablity via Simultaneous, Dual, Stable Isotope Administration: Bioequivalence Implications", *The Journal of Clinical Pharmacology*, vol. 39, pp. 817-825, 1999.

Tonn, et al., "Simultaneous Analysis of Diphenhydramine and a Stable Isotope Analog ($^2H_{10}$)Diphenhydramine Using Capillary Gas Chromatography with Mass Selective Detection in Biological Fluids from Chronically Instrumented Pregnant Ewes", *Biological Mass Spectrometry*, vol. 22, pp. 633-642, 1993.

Wolen, Robert L., "The Application of Stable Isotopes to Studies of Drug Bioabailablity and Bioequivalence", *The Journal of Clinical Pharmacology*, vol. 26, pp. 419-424, 1986.

Liu et al., "Deuterium in Drugs for Cardiovascular Disease: Design and Synthesis of Deuterated Cilostazol and Ranolazine Analogs with Enhanced Metabolic Stability," Concert Pharmaceuticals, Inc., Lexington, MA, 2010, 1 page.

* cited by examiner

ANALOGUES OF CILOSTAZOL

CROSS-REFERENCE TO PRIOR APPLICATIONS

This application claims priority under 35 USC 119 to U.S. Provisional Patent Application Ser. No. 61/203,577, filed Dec. 23, 2008. This application is also a continuation-in-part of co-pending U.S. patent application Ser. No. 12/150,107, filed Apr. 24, 2008, which claims priority under 35 USC 119 to expired U.S. Provisional Patent Application Ser. No. 60/926,100, filed Apr. 25, 2007. The entire teachings of these three applications are incorporated herein by reference.

BACKGROUND OF THE INVENTION

Many current medicines suffer from poor absorption, distribution, metabolism and/or excretion (ADME) properties that prevent their wider use. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, AB, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

Cilostazol is known by the chemical name 6-[4-(1-Cyclohexyl-1H-tetrazol-5-yl)butoxy]-3,4-dihydro-2(1H)-quinolinone. It is marketed under the tradename PLETAL® (Otsuka America Pharmaceutical, Inc.) in the United States for the treatment of intermittent claudication and under the tradename PLETAL® in Japan and South Korea for the treatment of chronic arterial occlusive disease, including diabetic complications of the peripheral vasculature. Cilostazol is also approved in Europe. The recommended daily dose is 100 mg BID, with 50 mg BID recommended if co-administering strong inhibitors of CYP3A4 and CYP2C19.

Cilostazol is a selective inhibitor of phosphodiesterase III with antiplatelet and antithrombotic activity. More specifically, cilostazol and several of its metabolites are cyclic AMP (cAMP) phosphodiesterase III inhibitors (PDE III inhibitors), inhibiting phosphodiesterase activity and suppressing cAMP degradation. This action results in an increase in cAMP in platelets and blood vessels, leading to inhibition of platelet aggregation and vasodilation, respectively. For example, cilostazol reversibly inhibits platelet aggregation induced by a variety of stimuli, including thrombin, ADP, collagen, arachidonic acid, epinephrine, and shear stress.

Currently, there are fifteen ongoing clinical trials for cilostazol in the areas of cerebral infarction, cerebrovascular disorders, atherosclerosis, diabetes mellitus complications, peripheral vascular disease, Reynaud's disease, intermittent claudication, ischemic heart disease, and acute coronary syndrome.

Additional trials are investigating cilostazol in combination with other therapeutics. For example, trials are investigating cilostazol in combination with aspirin in ischemic stroke patients ("Overcome Biochemical Aspirin Resistane [sic] Through Cilostazol Combination (ARCC)") and in combination with aspirin in chronic stroke patients studying the effect of aspirin plus cilostazol and aspirin alone on the progression of intracranial arterial stenosis, in 200 chronic stroke patients with 50-99% stenosis.

Despite the beneficial activities of cilostazol, there is a continuing need for new compounds to treat the aforementioned diseases and conditions.

SUMMARY OF THE INVENTION

This invention relates to novel compounds which are derivatives of the phosphodiesterase inhibitor, cilostazol and pharmaceutically acceptable salts thereof. This invention also provides pyrogen-free compositions comprising one or more compounds of the invention and the use of the disclosed compounds and compositions in methods of treating diseases and conditions that are treated by administration of a phosphodiesterase inhibitor, such as cilostazol. The invention also relates to the use of the disclosed compounds and compositions as reagents in analytical studies involving cilostazol.

DETAILED DESCRIPTION OF THE INVENTION

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

By "disease" is meant any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of cilostazol will inherently contain small amounts of deuterated isotopologues. The concentration of such naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Ganes, L Z et al., Comp Biochem Physiol A Mol Integr Physiol, 1998, 119:725.

In the compounds of the invention any atom not specifically designated as a particular isotope is meant to represent any stable isotope of that atom unless otherwise stated. Unless otherwise stated, when a position is designated specifically as "H" or "hydrogen," the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance at a specified position in a compound of this invention and the naturally occurring abundance of that isotope.

In other embodiments, a compound of this invention has an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof or of its ions. Isotopologues can differ in the level of isotopic enrichment at one or more positions and/or in the position(s) of isotopic enrichment.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts, particularly pharmaceutically acceptable salts, of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

Throughout the application all references to "a compound of Formula I," "a compound of Formula II," "a compound of the invention," or "a compound of claim" include, within the scope of each such term, synthetically feasible pharmaceutically acceptable salts of such compound(s).

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The disclosed compounds may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms.

When the stereochemistry of the disclosed compounds is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% optically pure. Percent optical purity by weight is the ratio of the weight of the enantiomer over the weight of the enantiomer plus the weight of its optical isomer.

When a disclosed compound is named or depicted by structure without indicating the stereochemistry, and has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer. When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" refer to deuterium.

"Stereoisomer" refers to both enantiomers and diastereomers.

"tert" refers to tertiary.

"US" refers to the United States of America.

As used herein, "each Y" variable includes, independently, any "Y" group (e.g., $Y^1$, $Y^2$, $Y^3$, and $Y^4$).

The term "perdeutero-cyclohexyl" refers to a cyclohexyl group where all the hydrogen atoms are replaced with deuterium (i.e., cyclohexyl-d11).

Therapeutic Compounds

The present invention provides compounds represented by Formula I:

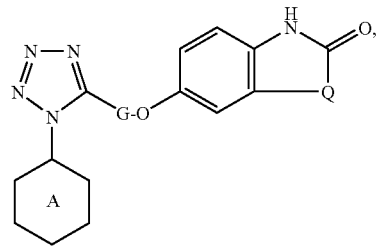

or a pharmaceutically acceptable salt thereof, wherein:

Ring A is a cyclohexyl ring containing 0-11 deuterium;

G is an n-butylene moiety containing 0-8 deuterium; and

Q is —$CH_2CH_2$— or —CH═CH— where one or more of the hydrogen atoms in Q is optionally replaced by deuterium, wherein when G is —$(CH_2)_4$— and Q is —$CH_2CH_2$— or —CH═CH—, then A is other than cyclohexyl or 2,2,6,6-tetradeuterocyclohexyl

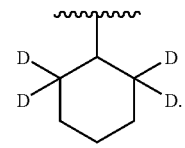

In one embodiment, G is selected from —$C(Y^1)(Y^2)$—$(CH_2)_2$—$C(Y^3)(Y^4)$-†, wherein each Y is independently selected from hydrogen and deuterium; and "†" represents the portion of G bound to oxygen in the compound. In one aspect of this embodiment, $Y^1$ and $Y^2$ are the same and $Y^3$ and $Y^4$ are the same. In another aspect embodiment, $Y^1$ and $Y^2$ are simultaneously deuterium or $Y^3$ and $Y^4$ are simultaneously deuterium. In a more specific aspect, $Y^1$ and $Y^2$ are simultaneously deuterium and $Y^3$ and $Y^4$ are simultaneously hydrogen. In another specific aspect $Y^1$ and $Y^2$ are simultaneously hydrogen and $Y^3$ and $Y^4$ are simultaneously deuterium. In still another specific aspect, each Y variable is deuterium. In yet another aspect each Y variable is hydrogen.

In another embodiment, G is —$(CD_2)_4$-.

Exemplary compounds of Formula I include those listed in Table 1, below, wherein G is —$(CH_2)_4$—:

TABLE 1

Exemplary compounds of Formula I.

| Compound | Ring "A" | Q |
|---|---|---|
| 100 | per-deuterocyclohexyl | -$CD_2CD_2$- |
| 101 | 4,4-dideuterocyclohexyl | -$CD_2CD_2$- |
| 102 | cyclohexyl | -$CD_2CD_2$- |
| 103 | per-deuterocyclohexyl | -$CD_2CH_2$— |
| 104 | 4,4-dideuterocyclohexyl | -$CD_2CH_2$— |
| 105 | cyclohexyl | -$CD_2CH_2$— |
| 106 | per-deuterocyclohexyl | —$CH_2CH_2$— |
| 107 | 4,4-dideuterocyclohexyl | —$CH_2CH_2$— |
| 108 | per-deuterocyclohexyl | -CD═CD- |

TABLE 1-continued

Exemplary compounds of Formula I.

| Compound | Ring "A" | Q |
|---|---|---|
| 109 | 4,4-dideuterocyclohexyl | -CD=CD- |
| 110 | per-deuterocyclohexyl | —CH=CH— |
| 111 | 4,4-dideuterocyclohexyl | —CH=CH— |

In another embodiment, the compound is selected from:

Compound 106

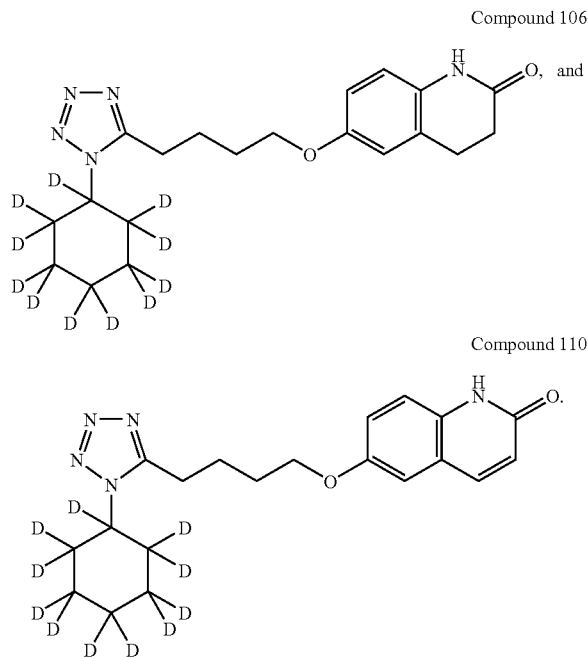

Compound 110

In another embodiment, the invention provides a compound of Formula I, wherein G is —(CH$_2$)$_4$; and ring A is dideuterated at least at each of the 3, 4 and 5 positions, the compound being represented by Formula II:

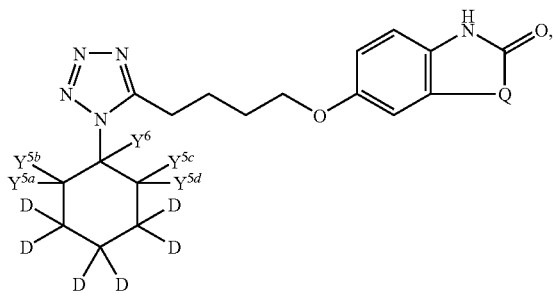

wherein each Y is independently selected from hydrogen and deuterium; and Q is as defined above (i.e., Q is —CH$_2$CH$_2$— or —CH=CH— where one or more of the hydrogen atoms in Q is optionally replaced by deuterium).

One embodiment provides a compound of Formula II other than Compound 106, Compound 108, or Compound 110.

Another embodiment provides a compound of Formula II, wherein at least one of Y$^{5a}$, Y$^{5b}$, Y$^{5c}$, Y$^{5d}$ and Y$^6$ is hydrogen.

In one embodiment, each Y$^5$ is the same. In one aspect of this embodiment, each Y$^5$ is deuterium and Y$^6$ is deuterium. In another aspect each Y$^5$ is deuterium and Y$^6$ is hydrogen. In still another aspect, each Y$^5$ is hydrogen and Y$^6$ is hydrogen. In yet another aspect, each Y$^5$ is hydrogen and Y$^6$ is deuterium.

In another embodiment of Formula II, Q is selected from —CH$_2$—CH$_2$— and —CH=CH—. In one aspect of this embodiment, each Y$^5$ is deuterium. In another aspect of this embodiment, each Y$^5$ is hydrogen.

In yet another embodiment, the compound is a compound of Formula II selected from any one of the compounds set forth in Table 2, wherein each Y$^5$ is the same.

TABLE 2

Exemplary Compounds of Formula II.

| Compound | Each Y$^5$ | Y$^6$ | Q |
|---|---|---|---|
| 112 | H | H | —CH$_2$—CH$_2$— |
| 113 | H | H | —CH=CH— |
| 114 | D | H | —CH$_2$—CH$_2$— |
| 115 | D | H | —CH=CH— |

In another set of embodiments, any atom not designated as deuterium in any of the embodiments set forth above is present at its natural isotopic abundance.

Compositions

In another embodiment, the invention also provides pyrogen-free pharmaceutical compositions comprising an effective amount of a compound of Formula I or Formula II, or a pharmaceutically acceptable salt thereof and a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J Hauss, ed. Informa Healthcare, 2007; and "Role of Lipid Excipients in Modifying Oral and Parenteral Drug Delivery: Basic Principles and Biological Examples," Kishor M Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, *Remington's Pharmaceutical Sciences*, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Pharmaceutical compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Pharmaceutical compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, TWEEN 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at rt but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz, J. D. and Zaffaroni, A. C., U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the patient compositions at the site of interest, such as injection, use of catheters, trocars, projectiles, pluronic gel, stents, sustained drug release polymers or other device which provides for internal access.

Thus, according to yet another embodiment, the compounds and compositions of this invention may be incorporated into coating compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886, 026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting the device with the coating composition described above. It will be obvious to those skilled in the art that the coating of the device will occur prior to implantation into a mammal.

According to another embodiment, the invention provides a method of impregnating an implantable drug release device comprising the step of contacting the drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that the compound is therapeutically active.

According to another embodiment, the invention provides an implantable drug release device impregnated with or containing a compound or a composition comprising a compound of this invention, such that the compound is released from the device and is therapeutically active.

Where an organ or tissue is accessible because of surgery, such organ or tissue may be bathed in a medium containing a composition of this invention, a composition of this invention may be painted onto the organ, or a composition of this invention may be applied in any other convenient way.

Examples for formulations and compositions relating to the compounds of this invention are described in U.S. Pat. Nos. 7,144,585, 6,923,988 and 6,720,001.

In another embodiment, a pharmaceutical composition of this invention further comprises one or more second therapeutic agents. In one embodiment, the second therapeutic agent is one or more additional compounds of the present invention. In one embodiment, each of the two or more compounds of the invention present in such compositions differs from all others in the positions(s) of isotopic enrichment. Commonly, such a composition comprises three, four, five or more different compounds of this invention.

In another embodiment, the choice of second therapeutic agent can be made from any second therapeutic agent known to be useful for co-administration with Compound 1. Examples of such agents and the conditions and diseases for which each may be used in conjunction with a compound of this invention include antiplatelet agents (e.g., aspirin and clopidogrel) in the treatment of stroke patients, and probucol.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 h of one another, consecutively or simultaneously).

As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich, et al., Cancer Chemother. Rep., 1966, 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 20 mg/day to about 400 mg/day. Administration can be in one or more doses per day (e.g., multiple doses). When multiple doses are used, the amount of each dose can be the same or different.

In a particular embodiment, an effective amount of a compound of this invention can range from about 20 mg/day to about 200 mg/day, from about 25 mg/day to about 200 mg/day, from about 30 mg/day to about 200 mg/day, from about 35 mg/day to about 200 mg/day, from about 40 mg/day to bout 200 mg/day, from about 45 mg/day to about 200 mg/day, from about 50 mg/day to about 200 mg/day. For example, an effective amount per day can be about 20 mg/day, 25 mg/day, 30 mg/day, or about 35 mg/day, or about 40 mg/day, or about 45 mg/day, or about 50 mg/day, or about 55 mg/day, or about 60 mg/day, or about 65 mg/day, or about 70 mg/day or about 75 mg/day, or about 80 mg/day, or about 85 mg/day, or about 90 mg/day, or about 95 mg/day, or about 100 mg/day, or about 150 mg/day, or about 200 mg/day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells, et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

Some of the second therapeutic agents referenced above may act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

The invention also provides a method of treating a disease that is susceptible to treatment by an antagonist of the phosphodiesterase III comprising the step of administering to a patient in need thereof an effective amount of a compound of Formula I or II or a pharmaceutical composition of this invention comprising a compound of Formula I or II and a pharmaceutically acceptable carrier.

Diseases or conditions susceptible to treatment by inhibition of phosphodiesterase III include, but are not limited to: chronic arterial occlusive disease, diabetic mellitus complications (e.g., complication of peripheral), intermittent claudication, intimal proliferation, restenosis, intracranial arterial stenosis, recurrent strokes, cerebral infarction, cerebrovascular disorders, atherosclerosis, atherothrombosis complications, peripheral vascular disease, Reynaud's Disease, sexual dysfunction, ulcers, cerebral circulation impairment, thrombolytic disorders, inflammation, hypotension, asthma, ischemic heart disease, coronary heart disease and acute coronary syndrome.

In a particular embodiment, the method of the invention is used to treat chronic arterial occlusive disease, intermittent claudication or stroke in a patient in need thereof comprising administering to the patient an effective amount of a compound of Formula I or II or a pharmaceutical composition comprising a compound of Formula I or II and a pharmaceutically acceptable carrier.

In another particular embodiment, the method of the invention is used to treat a patient suffering from or susceptible to Type 2 diabetes or metabolic syndrome X.

Methods delineated herein also include those wherein the patient is identified as in need of a particular stated treatment. Identifying a patient in need of such treatment can be in the judgment of a patient or a health care professional and can be subjective (e.g., opinion) or objective (e.g., measurable by a test or diagnostic method).

In another embodiment, the above methods of treatment comprise the further step of co-administering to the patient one or more second therapeutic agents. The choice of second therapeutic agent may be made from one or more additional compounds of the invention, or any second therapeutic agent known to be useful for co-administration with cilostazol. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In one embodiment, the second therapeutic agent is selected from aspirin, clopidogrel or ao combination thereof, and the patient is suffering from or susceptible to stroke or has recently been implanted with a drug-eluting stent.

In another embodiment, the second therapeutic agent is probucol, and the patient is suffering from or susceptible to type 2 diabetes or metabolic syndrome X.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to the patient at another time during a course of treatment.

Effective amounts of these second therapeutic agents are well known to those skilled in the art and guidance for dosing may be found in patents and published patent applications referenced herein, as well as in Wells, et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a patient, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

When the compounds, pharmaceutically acceptable salts thereof, compositions and pharmaceutical compositions of this invention are co-administered with another antiplatelet agent (e.g., aspirin or clopidogrel), the patient benefit from reduction of platelet aggregation that leads to other disorders.

In yet another aspect, the invention provides a compound of Formula I or II, a pharmaceutically acceptable salt thereof, or a pharmaceutical composition of Formula I or II, alone or together with one or more of the above-described second therapeutic agents for treatment or prevention in a patient of a disease, disorder or symptom set forth above. In a particular embodiment the disease is stroke. In a more particular embodiment, the disease is stroke and the second agent is aspirin or clopidogrel.

In other aspects, the methods herein include those further comprising monitoring patient response to the treatment administrations. Such monitoring can include periodic sampling of patient tissue, fluids, specimens, cells, proteins, chemical markers, genetic materials, etc. as markers or indicators of the treatment regimen. In other methods, the patient is prescreened or identified as in need of such treatment by assessment for a relevant marker or indicator of suitability for such treatment.

In another embodiment, the invention provides a method of modulating the activity of phosphodiesterase III in a cell, comprising contacting a cell with one or more compounds of Formula I or II, a pharmaceutically acceptable salt thereof, or pharmaceutical compositions of Formula I or II as described herein.

Pharmaceutical Kits

The present invention also provides kits for use to treat chronic arterial occlusive disease, diabetic mellitus complications (e.g., complication of peripheral vasculature), intermittent claudication, intimal proliferation, restenosis, intracranial arterial stenosis, recurrent strokes, cerebral infarction, cerebrovascular disorders, arthrosclerosis, atherothrombosis complications, peripheral vascular disease, Reynaud's Disease, sexual dysfunction, ulcers, cerebral circulation impairment, thrombolytic disorders, inflammation, hypotension, asthma, ischemic heart disease, coronary heart disease and acute coronary syndrome.

These kits comprise (a) a pharmaceutical composition comprising a compound of Formula I or II, a pharmaceutically acceptable thereof or a composition of Formula I or II, wherein the pharmaceutical composition is in a container; and (b) instructions describing a method of using the pharmaceutical composition to treat chronic arterial occlusive disease, diabetic mellitus complications (e.g., complication of peripheral vasculature), intermittent claudication, intimal proliferation, restenosis, intracranial arterial stenosis, recurrent strokes, cerebral infarction, cerebrovascular disorders, arthrosclerosis, atherothrombosis complications, peripheral vascular disease, Reynaud's Disease, sexual dysfunction, ulcers, cerebral circulation impairment, thrombolytic disorders, inflammation, hypotension, asthma, ischemic heart disease, coronary heart disease and acute coronary syndrome.

The container can be any vessel or other sealed or sealable apparatus that can hold the pharmaceutical composition. Examples include bottles, ampules, divided or multi-chambered holders bottles, wherein each division or chamber comprises a single dose of the composition, a divided foil packet wherein each division comprises a single dose of the composition, or a dispenser that dispenses single doses of the composition. The container can be in any conventional shape or form as known in the art which is made of a pharmaceutically acceptable material, for example, a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example, a conventional cardboard box would not generally be used to hold a liquid suspension. It is feasible that more than one container can be used together in a single package to market a single dosage form. For example, tablets may be contained in a bottle, which is in turn contained within a box. In on embodiment, the container is a blister pack.

The kit can additionally comprise a memory aid of the type containing information and/or instructions for the physician, pharmacist or patient. Such memory aids include numbers printed on each chamber or division containing a dosage that corresponds with the days of the regimen which the tablets or capsules so specified should be ingested, or days of the week printed on each chamber or division, or a card which contains the same type of information. For single dose dispensers, memory aids further include a mechanical counter which indicates the number of daily doses that have been dispensed and a battery-powered micro-chip memory coupled with a liquid crystal readout and/or audible reminder signal which, for example, reads out the date that the last daily dose has been taken and/or reminds one when the next dose is to be taken. Other memory aids useful in such kits are a calendar printed on a card, as well as other variations that will be readily apparent.

The kits of this invention can also comprise a device to administer or to measure out a unit dose of the pharmaceutical composition. Such device may include an inhaler if the composition is an inhalable composition; a syringe and needle if the composition is an injectable composition; a syringe, spoon, pump, or a vessel with or without volume markings if the composition is an oral liquid composition; or any other measuring or delivery device appropriate to the dosage formulation of the composition present in the kit.

Synthetic Procedures

The synthesis of compounds of Formula I or II can be readily achieved by synthetic chemists of ordinary skill. Relevant procedures are disclosed, for instance in: U.S. Pat. No. 4,277,479; International Publication Nos. WO2004/062571 and WO20042014283; Japanese Applications JP2005350474 and JP2004506043; and Chinese Applications CN1002-2602 20051226 and CN1002-8804 20050815.

Additionally, similar chemistry can be found in Occhiato, E G et al., Journal of Medicinal Chemistry, 2004, 47(14): 3546-3560, in JP 2000229944A, and in *Preparation of 6-hydroxy-2-oxo-1,2,3,4-tetrahydroquinoline*, by Lee, Byon Suku; Park, In Kyu; Shin, Sun Fun, Jpn. Kokai Tokkyo Koho (2000).

Such methods can be carried out utilizing corresponding deuterated and optionally, other isotope-containing reagents to synthesize the compounds delineated herein, or invoking standard synthetic protocols known in the art for introducing isotopic atoms to a chemical structure.

A convenient method for synthesizing compounds of Formula I is depicted in the Scheme 1 below. While Scheme 1 is illustrated using perdeutero-cyclohexanol as the starting material 10 to prepare Compound 106, the process can be generalized for cyclohexanol ring A groups having other levels of deuteration. Suitable methods for preparing intermediates useful in the synthesis of the compounds of Formula I are depicted in Schemes 2-3 below.

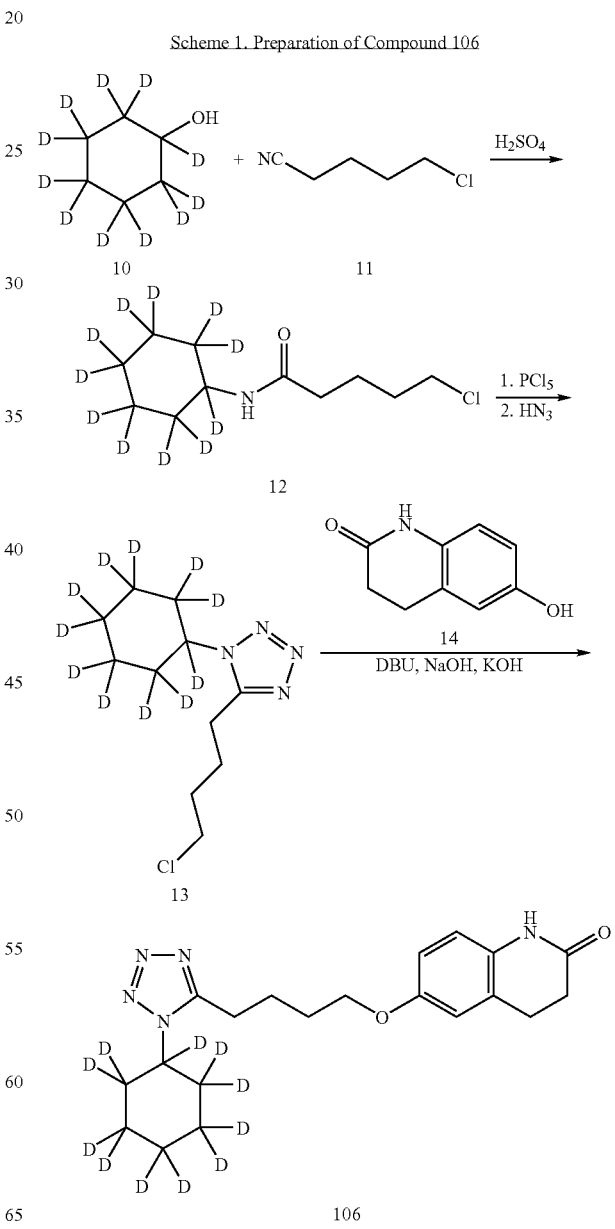

Scheme 1. Preparation of Compound 106

In Scheme 1 a deuterated alcohol such as commercially-available cyclohexan-d11-ol 10 is treated with commercially-available 5-chlorovaleronitrile 11 (or appropriately-deuterated versions thereof) in the presence of sulfuric acid to yield amide 12. Treatment with phosphorus pentachloride, followed by cyclization with hydrazoic acid affords chloride 13. Alkylation of commercially-available 3,4-dihydro-6-hydroxy-2(1H)-quinolinone 14 in the presence of DBU, NaOH and KOH affords desired deuterated compounds such as 106.

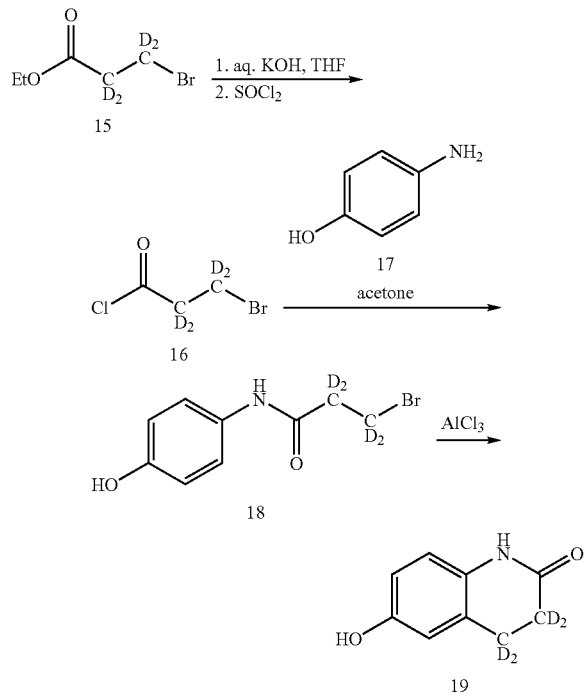

Scheme 2 depicts the synthesis of deuterated lactam 19 which may be incorporated into the synthetic route of Scheme 1 to produce other desired deuterated compounds. As shown in Scheme 2, commercially-available ethyl 3-bromopropionate-2,2,3,3-d4 15 is hydrolyzed with aqueous KOH and is then converted to the acid chloride 16 via treatment with thionyl chloride. Acylation of commercially-available 4-aminophenol 17 affords amide 18. Friedel-Crafts reaction with aluminum trichloride provides desired deuterated lactam 19.

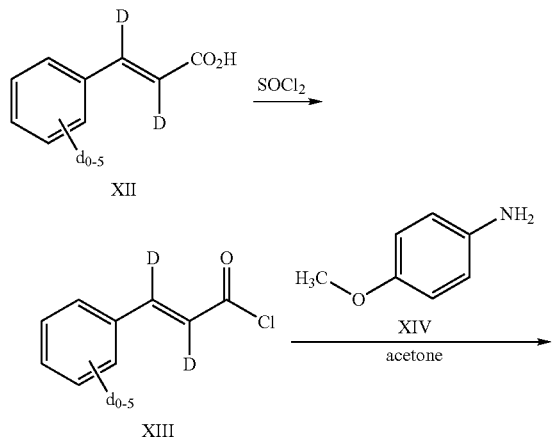

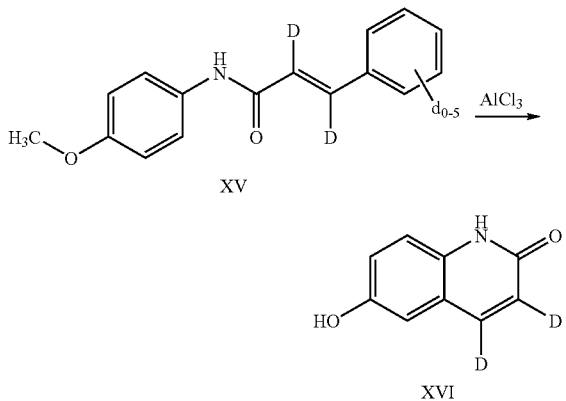

Scheme 3 shows the preparation deuterated lactam intermediate 24. 24 may be produced from deuterated carboxylic acid 20 in a manner similar to that of Wang, T C et al., Synthesis, 1997, (1): 87-90, and then be incorporated into the synthetic route of Scheme 1 to produce other desired deuterated compounds.

Additional methods of synthesizing compounds of Formula I or II and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

A description of example embodiments of the invention follows.

EXAMPLES

Example 1

Synthesis of 6-(4-(1-(Cyclohexyl-d$_{11}$)-1H-tetrazol-5-yl) butoxy)-3,4-dihydroquinolin-2(1H)-one (Compound 106). Compound 106 was prepared according to Scheme 4 below.

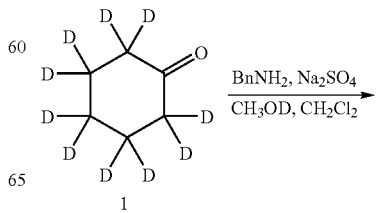

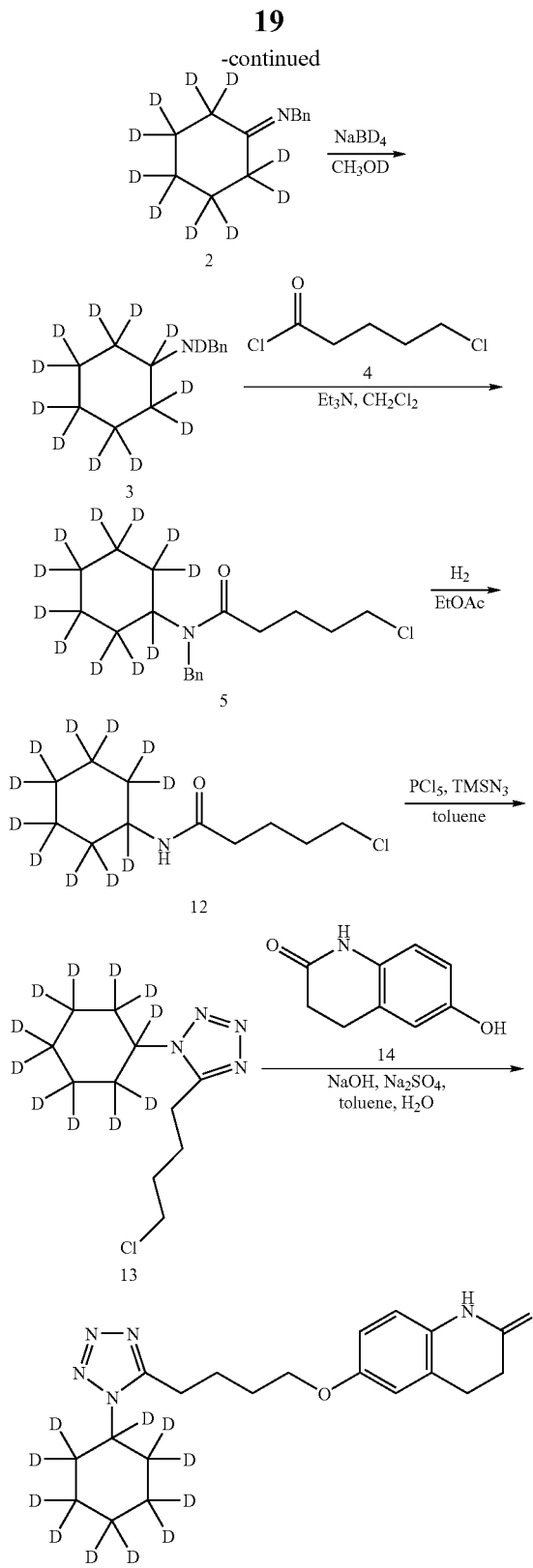

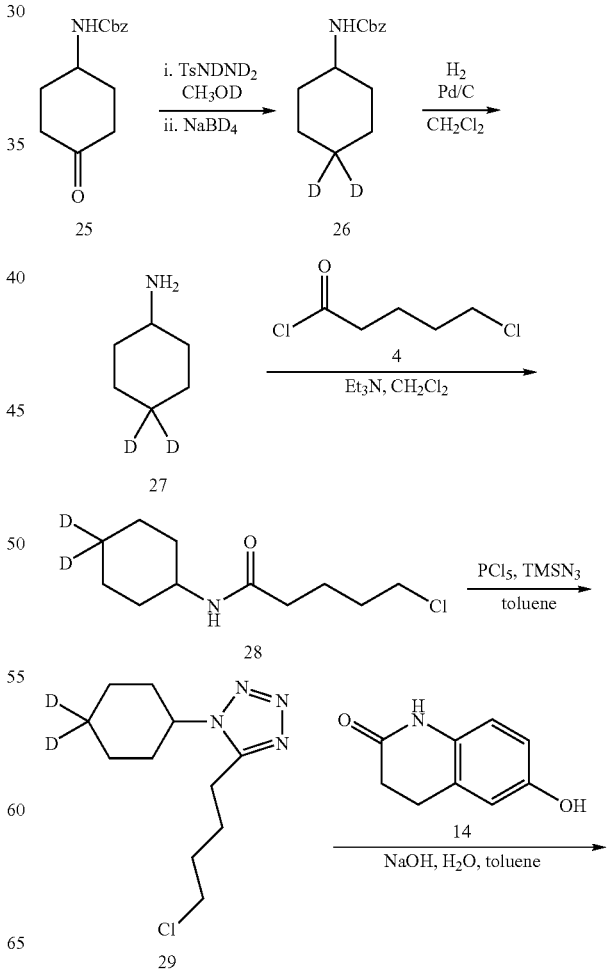

Synthesis of 6-(4-(1-(cyclohexyl-d₁₁)-1H-tetrazol-5-yl)butoxy)-3,4-dihydroquinolin-2(1H)-one (Compound 106).

As depicted in Scheme 4 above, and in a similar manner to Compound 107 shown below, commercially-available cyclohexanone-d10 (1) was converted via a six-step sequence into desired Compound 106. $^1$H-NMR (300 MHz, CDCl$_3$): δ 1.87-1.99 (m, 2H), 2.00-2.07 (m, 2H), 2.59-2.64 (m, 2H), 2.90-2.96 (m, 4H), 3.98 (t, J=5.9, 2H), 6.69-6.72 (m, 3H), 7.98 (s, 1H). $^{13}$C-NMR (75 MHz, CDCl$_3$): δ 23.02, 24.01, 25.73, 28.54, 30.62, 67.54, 113.09, 114.48, 116.04, 125.14, 130.84, 153.50, 154.78, 171.05. HPLC (method: Waters Atlantis T3 2.1×50 mm 3 μm C18-RP column-gradient method 5-95% ACN+0.1% formic acid in 14 min (1.0 mL/min) with 4 min hold at 95% ACN; Wavelength: 305 nm): retention time: 6.26 min; 99.0% purity. MS (M+H): 381.3. Elemental Analysis (C$_{20}$H$_{14}$D$_{11}$N$_5$O$_2$): Calculated: C=63.14; H=7.15; N=18.41. Found: C=62.80; H=7.25; N=18.20.

Example 2

Synthesis of 6-(4-(1-(4,4-d$_2$-Cyclohexyl)-1H-tetrazol-5-yl)butoxy)-3,4-dihydroquinolin-2(1H)-one (Compound 107). Compound 107 was prepared as outlined in Scheme 5 below. Details of the synthesis are set forth below.

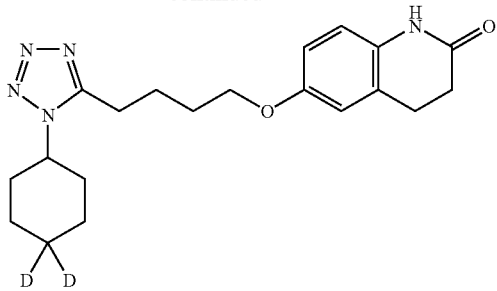

Compound 107

Synthesis of benzyl-(4,4-d$_2$-cyclohexyl)carbamate (26). N,N,N-d$_3$-(p-toluenesulfonyl)hydrazine (11.8 g, 63 mmol) was added to a solution of benzyl 4-oxocyclohexylcarbamate 25 (15 g, 63 mmol) in CH$_3$OD (180 mL). The reaction mixture was stirred at room temperature (rt) for 1 hour (h) with a white solid precipitating. The mixture was cooled to 0° C., and sodium borodeuteride (11.4 g, 315 mmol) was added to the reaction mixture in portions. After gas evolution ceased, the reaction mixture was heated at reflux until a clear solution was obtained (0.5 h). The reaction mixture was cooled to rt and stirred overnight. The reaction mixture was concentrated under reduced pressure and water (1 L) and methylene chloride (500 mL) were added to the residue. The aqueous layer was separated and extracted with methylene chloride (3×300 mL). The combined organic phases were washed with brine (200 mL), dried over sodium sulfate (100 g) and concentrated under reduced pressure. The crude product was purified by chromatography on silica gel, eluting with heptanes/ethyl acetate (5:1), to give 12.5 g (88%) of benzyl (4,4-d$_2$-cyclohexyl)carbamate 26 as a white solid. $^1$H NMR (CDCl$_3$) δ: 7.38 (m, 5H), 5.08 (s, 1H), 4.62 (s, 1H), 3.53 (m, 1H), 1.92 (m, 2H), 1.71 (m, 2H), 1.32 (m, 2H), 1.14 (2H); MS (M+H): 236.3.

Synthesis of 4,4-d$_2$-cyclohexylamine (27). A mixture of benzyl (4,4-d$_2$-cyclohexyl)carbamate 26 (4 g, 17 mmol) in methylene chloride (60 mL) and 10% Pd—C (2 g) was hydrogenated (shaken) overnight at 3 Bar H$_2$ pressure. The mixture was filtered through Celite and the pad washed with methylene chloride (200 mL). The filtrate was concentrated by distillation at atmospheric pressure to give crude 4,4-d$_2$-cyclohexylamine 27 that was used directly for the next reaction.

Synthesis of 5-chloro-N-(4,4-d$_2$-cyclohexyl)pentanamide (28). A solution of crude 4,4-d$_2$-cyclohexylamine 27 (approximately 16.8 mmol) and triethylamine (2.4 mL, 18.5 mmol) in methylene chloride (20 mL) was cooled in an ice-bath and 5-chlorovaleroyl chloride 4 (2 mL, 18.5 mmol) was added dropwise. The reaction mixture was allowed to warm to rt and was stirred overnight. The reaction mixture was diluted with methylene chloride (50 mL) and washed consecutively with saturated sodium bicarbonate solution, water, and brine. The organic solution was dried over sodium sulfate, filtered and concentrated under reduced pressure. The crude product was purified by column chromatography on silica gel, eluting with heptanes/ethyl acetate: (2:1 to 1:1) to give 650 mg (18% over 2 steps) of 5-chloro-N-(4,4-d$_2$-cyclohexyl)pentanamide 28. $^1$H-NMR (300 MHz, CDCl$_3$): δ 5.36 (s, 1H), 3.78 (m, 2H), 3.56 (t, 2H), 2.22 (t, 2H), 1.82 (m, 8H), 1.32 (m, 2H), 1.12 (m, 2H); MS (M+H): 220.1.

Synthesis of 5-(4-chlorobutyl)-1-(4,4-d$_2$-cyclohexyl)-1H-tetrazole (29). Phosphorous pentachloride (806 mg, 3.86 mmol) was added at rt to a solution of 5-chloro-N-(4,4-d$_2$-cyclohexyl)pentanamide 28 (650 mg, 2.97 mmol) in toluene (15 mL). After the reaction mixture was stirred for 3 h at rt, trimethylsilyl azide (0.57 mL, 4.3 mmol) was added. The reaction mixture was stirred at rt overnight. Water (15 ml) was added to the reaction mixture, the phases were separated, and the aqueous layer was extracted with toluene (3×15 mL). The combined organic phases were washed with brine, dried over sodium sulfate and concentrated under reduced pressure to give 640 mg (90%) of 29 as clear oil. $^1$H NMR (CDCl$_3$) δ: 4.18 (m, 1H), 3.61 (t, 2H), 2.92 (t, 2H), 2.00 (m, 10H), 1.43 (m, 2H). MS (M+H): 245.3.

Synthesis of 6-(4-(1-(4,4-d$_2$-cyclohexyl)-1H-tetrazol-5-yl)butoxy)-3,4-dihydroquinolin-2(1H)-one (Compound 107). To a mixture of 6-hydroxy-3,4-dihydroquinoline-2-one 14 (471 mg, 2.89 mmol) and sodium hydroxide (116 mg, 2.89 mmol) in water (10 mL) was added toluene (1.6 mL), 5-(4-chlorobutyl)-1-(4,4-d$_2$-cyclohexyl)-1H-tetrazole 29 (640 mg, 2.62 mmol), sodium sulfate (490 mg) and Aliquot® 336 (0.062 mL). The reaction mixture was heated at reflux for 2-3 days. The mixture was cooled to rt and diluted with water (20 mL) and toluene (20 mL). The aqueous phase was extracted with toluene (3×20 mL). The combined organic phases were washed with brine, dried over sodium sulfate and concentrated under reduced pressure. The crude product was purified by automated column chromatography on an Analogix system using 0-100% ethyl acetate/heptanes to give 220 mg of Compound 107 as a white solid. $^1$H-NMR (300 MHz, CDCl$_3$): δ 1.40-1.43 (m, 2H), 1.87-2.06 (m, 10H), 2.58-2.63 (m, 2H), 2.90-2.96 (m, 4H), 3.98 (t, J=5.9, 2H), 4.10-4.14 (m, 1H), 6.68-6.72 (m, 3H), 7.98 (s, 1H). $^{13}$C-NMR (75 MHz, CDCl$_3$): δ 23.03, 24.02, 25.13, 25.74, 28.55, 30.63, 57.62, 67.54, 113.10, 114.48, 116.05, 125.14, 130.85, 153.52, 154.79, 171.06. HPLC (method: Waters Atlantis T3 2.1×50 mm 3 μm C18-RP column-gradient method 5-95% ACN+ 0.1% formic acid in 14 min (1.0 mL/min) with 4 min hold at 95% ACN; Wavelength: 254 nm): retention time: 6.29 min; 98.6% purity. MS (M+H): 372.3. Elemental Analysis (C$_{20}$H$_{25}$D$_2$N$_5$O$_2$): Calculated: C=64.67; H=7.33; N=18.85. Found: C=64.22; H=7.48; N=18.56.

Example 3

Synthesis of 6-(4-(1-(4,4-d$_2$-Cyclohexyl)-1H-tetrazol-5-yl)butoxy)-3,3,4,4-d$_4$-dihydroquinolin-2(1H)-one (Compound 101). Compound 101 was prepared as outlined in Scheme 6 below. Details of the synthesis are set forth below.

Scheme 6. Preparation of Compound 101

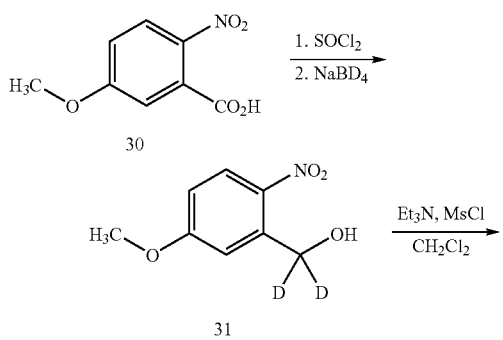

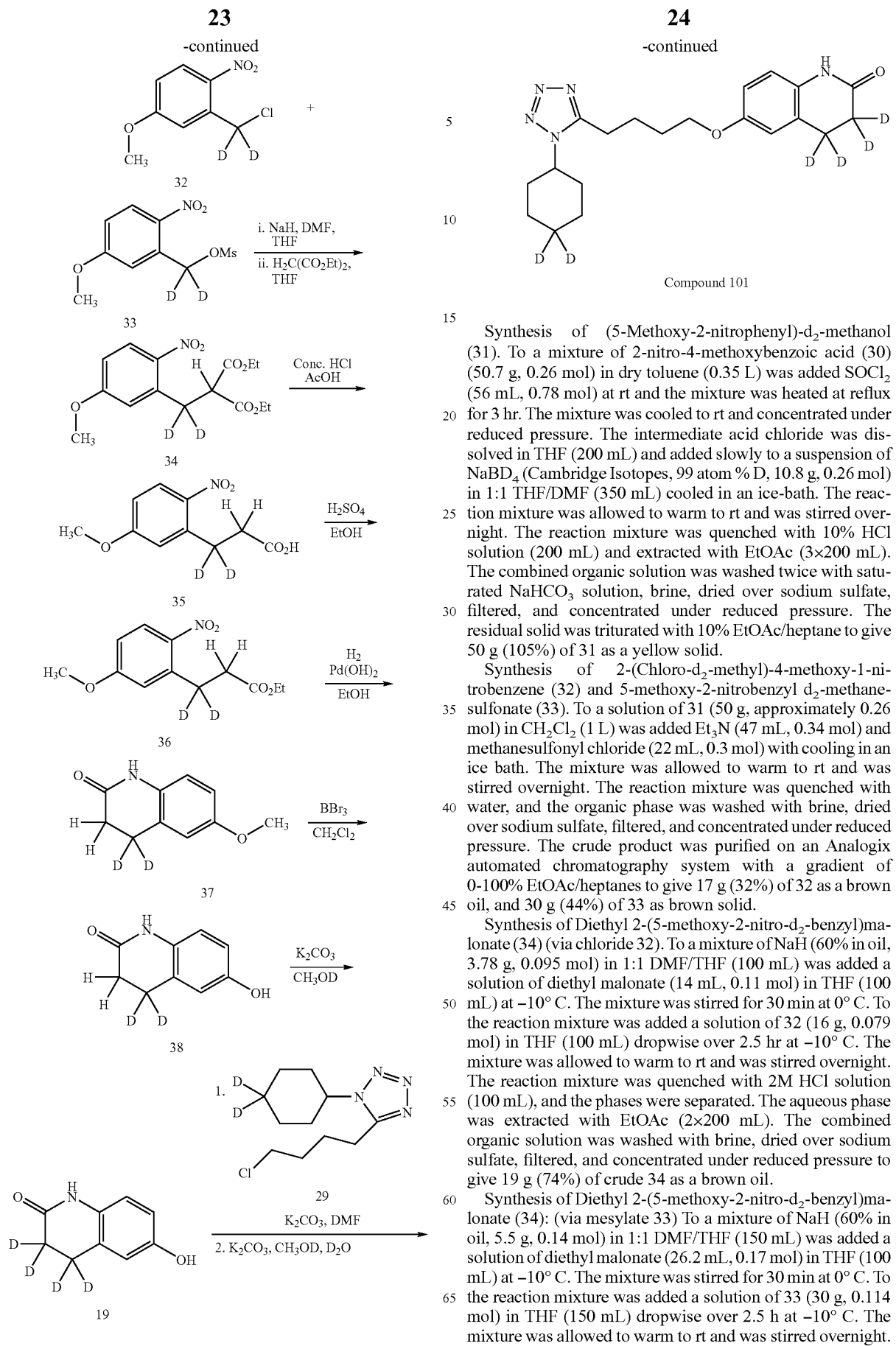

Compound 101

Synthesis of (5-Methoxy-2-nitrophenyl)-$d_2$-methanol (31). To a mixture of 2-nitro-4-methoxybenzoic acid (30) (50.7 g, 0.26 mol) in dry toluene (0.35 L) was added $SOCl_2$ (56 mL, 0.78 mol) at rt and the mixture was heated at reflux for 3 hr. The mixture was cooled to rt and concentrated under reduced pressure. The intermediate acid chloride was dissolved in THF (200 mL) and added slowly to a suspension of $NaBD_4$ (Cambridge Isotopes, 99 atom % D, 10.8 g, 0.26 mol) in 1:1 THF/DMF (350 mL) cooled in an ice-bath. The reaction mixture was allowed to warm to rt and was stirred overnight. The reaction mixture was quenched with 10% HCl solution (200 mL) and extracted with EtOAc (3×200 mL). The combined organic solution was washed twice with saturated $NaHCO_3$ solution, brine, dried over sodium sulfate, filtered, and concentrated under reduced pressure. The residual solid was triturated with 10% EtOAc/heptane to give 50 g (105%) of 31 as a yellow solid.

Synthesis of 2-(Chloro-$d_2$-methyl)-4-methoxy-1-nitrobenzene (32) and 5-methoxy-2-nitrobenzyl $d_2$-methanesulfonate (33). To a solution of 31 (50 g, approximately 0.26 mol) in $CH_2Cl_2$ (1 L) was added $Et_3N$ (47 mL, 0.34 mol) and methanesulfonyl chloride (22 mL, 0.3 mol) with cooling in an ice bath. The mixture was allowed to warm to rt and was stirred overnight. The reaction mixture was quenched with water, and the organic phase was washed with brine, dried over sodium sulfate, filtered, and concentrated under reduced pressure. The crude product was purified on an Analogix automated chromatography system with a gradient of 0-100% EtOAc/heptanes to give 17 g (32%) of 32 as a brown oil, and 30 g (44%) of 33 as brown solid.

Synthesis of Diethyl 2-(5-methoxy-2-nitro-$d_2$-benzyl)malonate (34) (via chloride 32). To a mixture of NaH (60% in oil, 3.78 g, 0.095 mol) in 1:1 DMF/THF (100 mL) was added a solution of diethyl malonate (14 mL, 0.11 mol) in THF (100 mL) at −10° C. The mixture was stirred for 30 min at 0° C. To the reaction mixture was added a solution of 32 (16 g, 0.079 mol) in THF (100 mL) dropwise over 2.5 hr at −10° C. The mixture was allowed to warm to rt and was stirred overnight. The reaction mixture was quenched with 2M HCl solution (100 mL), and the phases were separated. The aqueous phase was extracted with EtOAc (2×200 mL). The combined organic solution was washed with brine, dried over sodium sulfate, filtered, and concentrated under reduced pressure to give 19 g (74%) of crude 34 as a brown oil.

Synthesis of Diethyl 2-(5-methoxy-2-nitro-$d_2$-benzyl)malonate (34): (via mesylate 33) To a mixture of NaH (60% in oil, 5.5 g, 0.14 mol) in 1:1 DMF/THF (150 mL) was added a solution of diethyl malonate (26.2 mL, 0.17 mol) in THF (100 mL) at −10° C. The mixture was stirred for 30 min at 0° C. To the reaction mixture was added a solution of 33 (30 g, 0.114 mol) in THF (150 mL) dropwise over 2.5 h at −10° C. The mixture was allowed to warm to rt and was stirred overnight.

The reaction was quenched with 2M HCl solution (100 mL) and the phases were separated. The aqueous phase was extracted with EtOAc (2×200 mL). The combined organic solution was washed with brine, dried over sodium sulfate, filtered, and concentrated under reduced pressure to give 40 g (108%) of crude 34 as a brown oil.

Synthesis of 3-(5-Methoxy-2-nitrophenyl)-3,3-$d_2$-propanoic acid (35). A mixture of 34 (19 g, 0.058 mol) in acetic acid (100 mL) and conc. HCl (35 mL) was heated at reflux for 8 hr. The reaction mixture was concentrated under reduced pressure to give crude 35 as a brown solid that was used in the next reaction without further purification.

Synthesis of Ethyl 3-(5-methoxy-2-nitrophenyl)-3,3-$d_2$-propanoate (36). A mixture of crude 35 (approximately 0.058 mol) and conc. $H_2SO_4$ (1 mL) in EtOH (0.5 L) was heated at reflux overnight to give crude 36. The crude solution was used directly in the next step.

Synthesis of 6-Methoxy-4,4-$d_2$-3,4-dihydroquinolin-2 (1H)-one (37). A mixture of crude 36 (approximately 0.058 mol) in EtOH (0.5 L) and 10% Pd(OH)$_2$/C (50% water) (1.2 g) was hydrogenated at 40 psi $H_2$ overnight. The mixture was filtered through a pad of Celite, washing the pad with ethanol (0.5 L). The filtrate was concentrated under reduced pressure, and the residue was diluted with EtOAc (0.5 L). The organic solution was washed with saturated NaHCO$_3$ solution (200 mL), and the aqueous phase was back-extracted with EtOAc (3×0.2 L). The combined organic solution was washed with brine, dried over sodium sulfate, filtered, and concentrated under reduced pressure to give crude 37 as brown solid.

Synthesis of 6-Hydroxy-4,4-$d_2$-3,4-dihydroquinolin-2 (1H)-one (38). To a solution of compound 37 (58 mmol) in $CH_2Cl_2$ (200 mL) was added 1M BBr$_3$ in $CH_2Cl_2$ (425 mL) at −78° C. The resulting mixture was allowed to warm to rt and was stirred overnight. The reaction mixture was quenched with water with cooling in an ice-bath. The precipitate was filtered, washed with water and dried in a vacuum oven at 60° C. to give 5.98 g (92% over 4 steps from 34) of 38 as a brown solid.

Synthesis of 6-Hydroxy-3,3,4,4-$d_4$-dihydroquinolin-2 (1H)-one (19). To a solution of 38 (5.98 g, 36 mmol) in methanol-d (Cambridge Isotopes, 99 atom % D, 60 mL) was added K$_2$CO$_3$ (11 g, 72 mmol) and the reaction mixture was refluxed overnight. The methanol was removed under reduced pressure, D$_2$O (Cambridge Isotopes, 99 atom % D, 50 mL) was added and the mixture was refluxed overnight. After cooling to rt, 1M DCl (Aldrich, 99 atom % D, 15 mL) was used to neutralize the reaction mixture. The precipitate was filtered, washed with D$_2$O and dried in a vacuum oven at 60° C. to give 4.5 g (75%) of 19 as a brown solid.

Synthesis of 6-(4-(1-(4,4-$d_2$-Cyclohexyl)-1H-tetrazol-5-yl)butoxy)-3,3,4,4-$d_4$-dihydroquinolin-2(1H)-one (Compound 101). To a solution of 19 and K$_2$CO$_3$ (2.2 g, 16 mmol) in DMF (40 mL) was added 29 (2 g, 9 mmol). The reaction mixture was heated at reflux overnight. After the mixture was cooled to rt, the solid was filtered and washed with EtOAc (100 mL). The filtrate was concentrated under reduced pressure and the crude product was purified on an Analogix automated chromatography system with a gradient of 0-100% EtOAc/heptanes to give 12 g (39%) of Compound 101 as a white solid. $^1$H NMR showed that the material had undergone some deuterium/hydrogen exchange during the alkylation. To re-exchange the hydrogen atoms for deuterium atoms, the solid was dissolved in methanol-d (Cambridge Isotopes, 99 atom % D, 20 mL). D$_2$O (Cambridge Isotopes, 99 atom % D, 20 mL) and K$_2$CO$_3$ (2.2 g, 16 mmol) were added and the reaction mixture was heated to reflux overnight. Methanol-d was removed under reduced pressure, the precipitated solid was filtered, washed with D$_2$O (30 mL) and heptane (30 mL) and dried in a vacuum oven at 60° C. to give 1.1 g (33%) of Compound 101. $^1$H-NMR (300 MHz, CDCl$_3$): δ 1.35-1.43 (m, 2H), 1.87-2.09 (m, 10H), 2.92 (t, J=7.3, 2H), 3.98 (t, J=5.9, 2H), 4.08-4.15 (m, 1H), 6.63-6.72 (m, 3H), 7.56 (s, 1H). HPLC (method: Waters Atlantis T3 2.1×50 mm 3 μm C18-RP column-gradient method 5-95% ACN+0.1% formic acid in 14 min (1.0 mL/min) with 4 min hold at 95% ACN; Wavelength: 254 nm): retention time: 6.26 min; 99.6% purity. MS (M+H): 376.2. Elemental Analysis (C$_{20}$H$_{21}$D$_6$N$_5$O$_2$.0.15H$_2$O): Calculated: C=63.52; H=7.28; N=18.52. Found: C=63.14; H=7.31; N=18.25.

Example 4

Synthesis of 6-(4-(1-(Cyclohexyl-$d_{11}$)-1H-tetrazol-5-yl)butoxy)-3,3,4,4-$d_4$-dihydroquinolin-2(1H)-one (Compound 100). Compound 100 was prepared as outlined in Scheme 7 below. Details of the synthesis are set forth below.

Scheme 7. Preparation of Compound 100

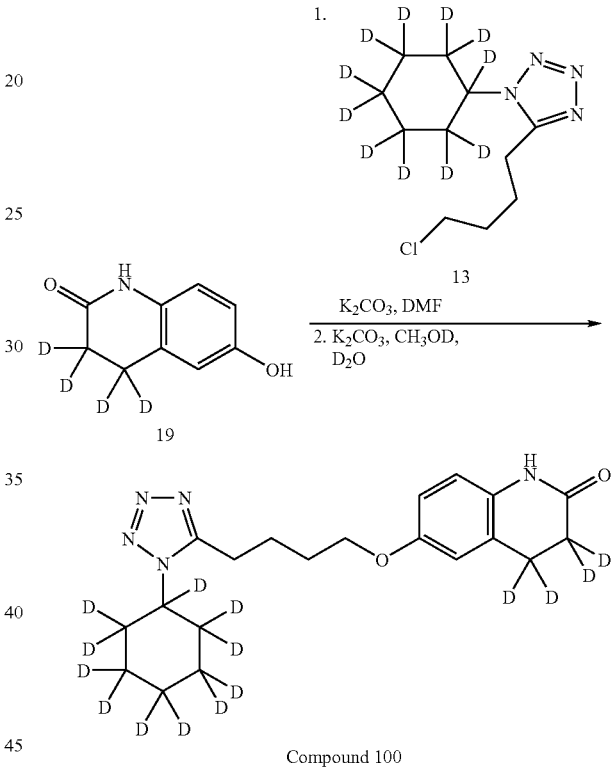

Compound 100

Synthesis of 6-(4-(1-(Cyclohexyl-$d_{11}$)-1H-tetrazol-5-yl)butoxy)-3,3,4,4-$d_a$-dihydroquinolin-2(1H)-one (Compound 100). To a mixture of 19 from Example 3 (1.5 g, 9 mmol) and K$_2$CO$_3$ (2.2 g, 16 mmol) in DMF (40 mL) was added 13 (2 g, 9 mmol). The reaction mixture was heated at reflux overnight. The mixture was cooled to rt, filtered, the solid washed with EtOAc (100 mL) and the filtrate concentrated under reduced pressure. The crude product was purified on an Analogix automated chromatography system with a gradient of 0-100% EtOAc/heptanes to afford 1.7 g (55%) of Compound 100 as white solid. $^1$H NMR showed that the material had undergone some deuterium/hydrogen exchange during the alkylation. To re-exchange the hydrogen atoms for deuterium atoms, the solid was dissolved in methanol-d (Cambridge Isotopes, 99 atom % D, 20 mL). D$_2$O (Cambridge Isotopes, 99 atom % D, 20 mL) and K$_2$CO$_3$ (2.2 g, 16 mmol) were added and the reaction mixture was heated to reflux overnight. Methanol-d was removed under reduced pressure, the precipitated solid was filtered, washed with D$_2$O (30 mL) and heptane (30 mL) and dried in a vacuum oven at 60° C. to give 1.6 g (33%) of Compound 100. $^1$H-NMR (300 MHz, CDCl$_3$): δ 1.87-1.94 (m, 2H), 1.99-2.07 (m, 2H), 2.92 (t, J=7.4, 2H), 3.98 (t, J=5.9, 2H), 6.68-6.72 (m, 3H), 7.91 (s, 1H). $^{13}$C-NMR (75 MHz, CDCl$_3$): δ 23.03, 24.02, 28.55, 67.55, 113.11, 114.53, 116.02, 125.02, 130.88, 153.50, 154.79, 171.05. HPLC (method: Waters Atlantis T3 2.1×50 mm 3 μm C18-RP column-gradient method 5-95% ACN+0.1% formic acid in 14 min (1.0 mL/min) with 4 min hold at 95% ACN; Wavelength: 305 nm): retention time: 6.23 min; 99.3% purity. MS (M+H): 385.2. Elemental Analysis (C$_{20}$H$_{12}$D$_{15}$N$_5$O$_2$): Calculated: C=62.48; H=7.08; N=18.22. Found: C=62.18; H=7.11; N=18.17.

Example 5

Synthesis of 6-(4-(1-(Cyclohexyl-d$_{11}$)-1H-tetrazol-5-yl)butoxy)-3,3,4,4-d$_2$-dihydroquinolin-2(1H)-one (Compound 110). Compound 110 was prepared as outlined in Scheme 8 below. Details of the synthesis are set forth below.

Scheme 8. Preparation of Compound 110

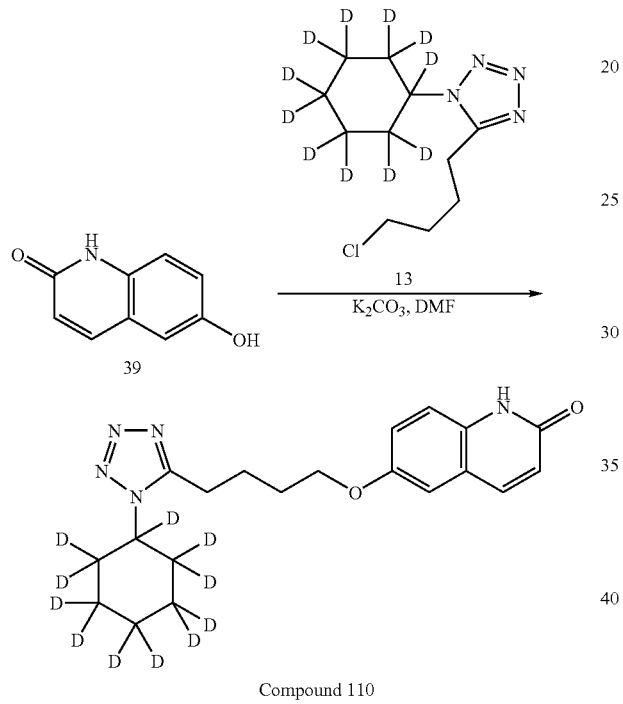

Synthesis of 6-(4-(1-(Cyclohexyl-d$_{11}$)-1H-tetrazol-5-yl)butoxy)-dihydroquinolin-2(1H)-one (Compound 110): To a solution of 2,6-dihydroxyquinoline (39, 710 mg, 4.5 mmol) and K$_2$CO$_3$ (1.1 g, 8 mmol) in DMF (20 mL) was added 13 from Example 1 (1 g, 9 mmol). The reaction mixture was heated at reflux overnight. After the mixture was cooled to rt the solid was filtered, washed with EtOAc (50 mL) and the filtrate concentrated under reduced pressure. The crude product was purified on an Analogix automated chromatography system with 0-100% EtOAc/heptanes to give 450 mg (29%) of Compound 110 as white solid. $^1$H-NMR (300 MHz, CDCl$_3$): δ 1.92-1.99 (m, 2H), 2.03-2.10 (m, 2H), 2.94 (t, J=7.3, 2H), 4.07 (t, J=5.8, 2H), 6.72 (d, J=9.6, 1H), 6.98 (d, J=2.6, 1H), 7.13 (dd, J$_1$=9.0, J$_2$=2.7, 1H), 7.32 (d, J=9.1, 1H), 7.74 (d, J=9.4, 1H), 11.72 (s, 1H). $^{13}$C-NMR (75 MHz, CDCl$_3$): δ 23.25, 24.19, 28.71, 67.88, 109.98, 117.47, 120.66, 120.70, 122.19, 133.25, 140.68, 153.69, 154.61, 163.92. HPLC (method: Waters Atlantis T3 2.1×50 mm 3 μm C18-RP column-gradient method 5-95% ACN+0.1% formic acid in 14 min (1.0 mL/min) with 4 min hold at 95% ACN; Wavelength: 305 nm): retention time: 6.06 min; 98.1% purity. MS (M+H): 379.2. Elemental Analysis (C$_{20}$H$_{14}$D$_{11}$N$_5$O$_2$): Calculated: C=63.47; H=6.66; N=18.51. Found: C=63.12; H=6.51; N=18.31.

Example 6

Synthesis of 6-(4-(1-(3,3,4,4,5,5-d$_6$-Cyclohexyl)-1H-tetrazol-5-yl)butoxy)-3,4-dihydroquinolin-2(1H)-one (Compound 112). Compound 112 was prepared as outlined in Scheme 9 below. Details of the synthesis are set forth below.

Scheme 9. Preparation of Compound 112

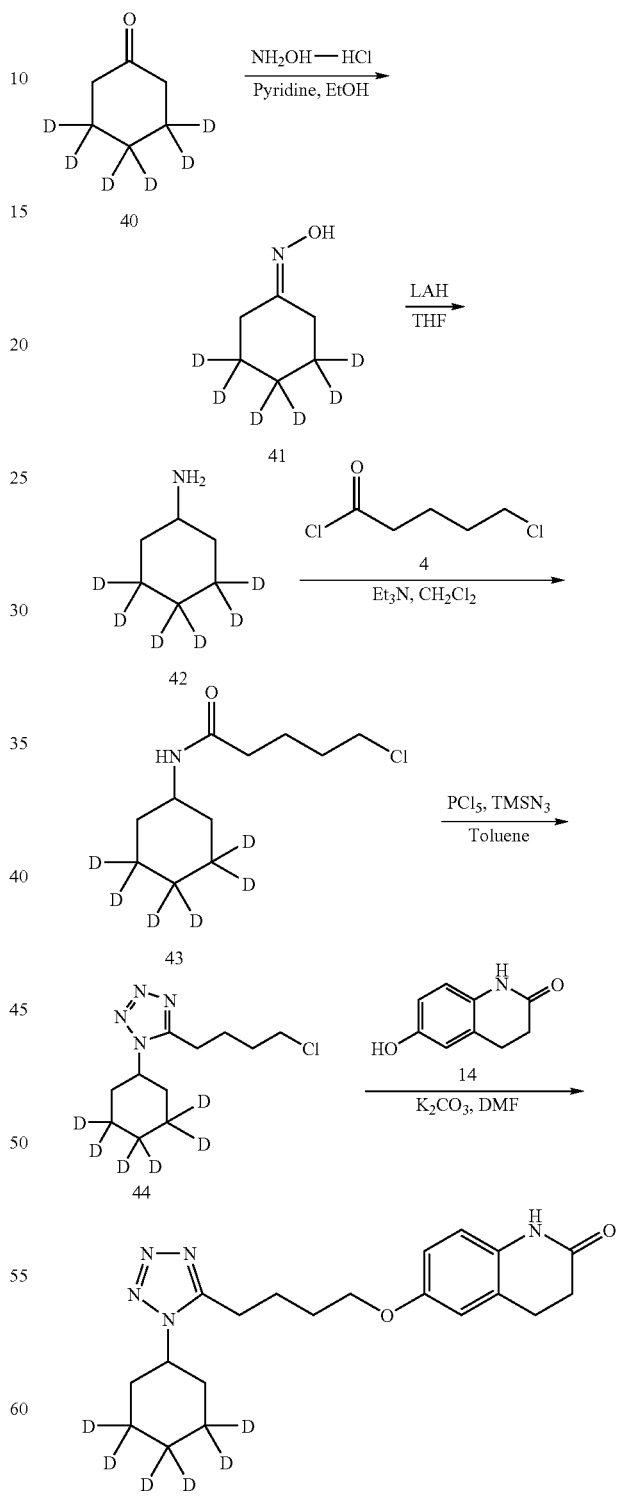

Synthesis of d$_6$-Cyclohexanone Oxime (41). To a solution of commercially available d$_6$-cyclohexanone 40 (CDN, 98 atom % D) (2.04 g, 19.6 mmol) and pyridine (1.74 mL, 21.6 mmol) in absolute ethanol (80 mL) was added $NH_2OH \cdot HCl$ (1.36 g, 19.6 mmol). The reaction was heated to reflux and stirred for 15 h. Upon completion, the reaction was cooled to rt, diluted with saturated $NaHCO_3$, filtered through Celite, and concentrated under reduced pressure. The resulting residue was diluted with water (100 mL) and extracted with dichloromethane (3×100 mL). The organic layers were combined, dried ($Na_2SO_4$), filtered and concentrated under reduced pressure to afford 41 (1.98 g, 85%) as an off-white solid that was used in the next step without further purification. MS (M+H): 120.3.

Synthesis of 3,3,4,4,5,5-$d_6$-Cyclohexyl amine (42). To a solution of oxime 41 (0.875 g, 7.34 mmol) in THF (5 mL) was added dropwise a 2M solution of LAH in THF (9.18 mL, 18.4 mmol) at rt. The reaction mixture was refluxed for 5 hr, cooled to rt and quenched by careful addition of DCM (50 mL) and 10 M NaOH (20 mL). The phases were separated and the aqueous phase extracted with DCM (3×50 mL). The combined organic solution was dried over sodium sulfate, filtered, and concentrated to approximately 50 mL total volume under reduced pressure. The solution of crude 42 was directly used in the next step.

Synthesis of 5-Chloro-N-(3,3,4,4,5,5-$d_6$-cyclohexylpentanamide (43). To a solution of crude 42 (7.34 mmol) and triethylamine (1.13 mL, 8.07 mmol) in DCM (50 mL) was added 5-chlorovalerylchloride (4; 943 L, 7.34 mmol) dropwise with cooling in an ice-bath. The reaction mixture was allowed to warm to rt and stirred for 15 h. The mixture was then diluted with DCM (50 mL) and washed with saturated sodium bicarbonate solution, water, and brine, dried over sodium sulfate and concentrated under reduced pressure to afford 43 (1.55 g, 95%) as a white solid which was used without further purification. MS (M+H): 224.2.

Synthesis of 5-(4-Chlorobutyl)-1-(3,3,4,4,5,5-$d_6$-cyclohexyl)-1H-tetrazole (44). To a solution of crude 43 (1.54 g, 6.88 mmol) in toluene (70 mL) was added phosphorous pentachloride (1.65 g, 7.91 mmol) at rt. After the reaction mixture had stirred at rt for 3 h, trimethylsilyl azide (1.18 mL, 8.94 mmol) was added and the reaction mixture stirred for 15 h. The reaction was then diluted with water (100 mL) and the resulting solution was extracted with toluene (3×100 mL). The combined organic layers were washed with brine, dried over magnesium sulfate, filtered, and concentrated under reduced pressure to afford 44 (1.66 g, 97%) as clear oil that solidified upon storage at −20° C. MS (M+H): 249.3.

Synthesis of 6-(4-(1-(3,3,4,4,5,5-$d_6$-Cyclohexyl)-1H-tetrazol-5-yl)butoxy)-3,4-dihydroquinolin-2(1H)-one (Compound 112). To a mixture of 14 (361 mg, 2.21 mmol) and $K_2CO_3$ (556 mg, 4.02 mmol) in DMF (7 mL) was added 44 (500 mg, 2.01 mmol). The reaction mixture was stirred at reflux for 15 h then cooled to rt. The solids were then removed by filtration, washed with EtOAc (100 mL), and the filtrate concentrated under reduced pressure and the crude product was purified on silica gel eluting with a gradient of 0-100% EtOAc/heptanes followed by 0-5% MeOH/DCM to afford Compound 112 (265 mg, 35%) as a white solid. $^1$H NMR (CDCl$_3$, 400 MHz): δ 8.80 (s, 1 H), 6.76-6.65 (m, 3 H), 4.11 (hept., 1 H, J=4.8 Hz), 3.97 (t, 2 H, J=6.0 Hz), 2.96-2.86 (m, 4 H), 2.65-2.55 (m, 2 H), 2.08-1.82 (m, 8 H); MS (M+H): 376.3.

Example 7

Synthesis of 6-(4-(1-(3,3,4,4,5,5-$d_6$-Cyclohexyl)-1H-tetrazol-5-yl)butoxy)-3,4-dihydroquinolin-2(1H)-one (Compound 113). Compound 113 was prepared as outlined in Scheme 10 below. Details of the synthesis are set forth below.

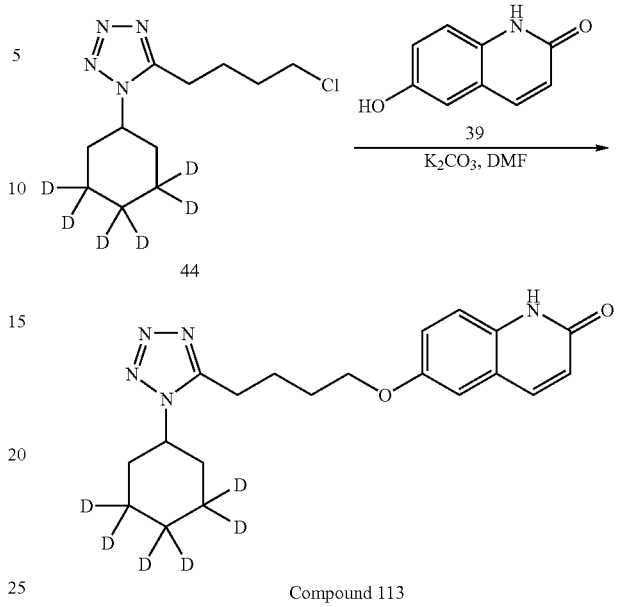

Scheme 10. Preparation of Compound 113

Compound 113

Synthesis of 6-(4-(1-(3,3,4,4,5,5-$d_6$-Cyclohexyl)-1H-tetrazol-5-yl)butoxy)-3,4-dihydroquinolin-2(1H)-one (Compound 113). To a solution of 2,6-dihydroxyquinoline (39) (Sigma-Aldrich; 260 mg, 1.61 mmol) and $K_2CO_3$ (400 mg, 2.90 mmol) in DMF (8 mL) was added 44 from Example 6 (800 mg, 3.22 mmol). The reaction mixture was stirred at reflux for 15 h. After the mixture was cooled to rt the solid was filtered, washed with EtOAc (50 mL) and the filtrate concentrated under reduced pressure. The crude product was purified on silica gel eluting with 0-100% EtOAc/heptanes followed by 0-5% MeOH/DCM to afford the desired product which was further purified via recrystallization (MeOH/EtOAc/heptane) to afford Compound 113 (112 mg, 19%) as a white solid. $^1$H NMR (CDCl$_3$, 400 MHz): δ 12.20 (s, 1 H), 7.75 (d, 1 H, J=9.6 Hz), 7.35 (d., 1 H, J=8.8 Hz), 7.13 (dd, 1 H, J=2.5, 8.8 Hz), 6.97 (d, 1 H, J=2.5 Hz), 6.72 (d, 1 H, J=9.6 Hz), 4.12 (hept., 1 H, J=4.8 Hz), 4.06 (t, 2 H, J=6.1 Hz), 2.94 (t, 2 H, J=7.3 Hz), 2.14-1.88 (m, 8H). MS (M+H): 374.3.

Biological Testing

Example 8

Determination of Metabolic Stability in Human Liver Microsomes. Human liver microsomes (20 mg/mL) were obtained from Xenotech, LLC (Lenexa, Kans.).

nicotinamide adenine dinucleotide phosphate, reduced form (NADPH), magnesium chloride ($MgCl_2$), and dimethyl sulfoxide (DMSO) were purchased from Sigma-Aldrich.

7.5 mM stock solutions of test compounds, as well as cilostazol and 7-ethoxycoumarin (as a positive control) were prepared in DMSO. The 7.5 mM stock solutions were diluted to 50 M in acetonitrile (ACN). The 20 mg/mL human liver microsomes were diluted to 0.625 mg/mL in 0.1 M potassium phosphate buffer, pH 7.4, containing 3 mM $MgCl_2$. The diluted microsomes were added to wells of a 96-well deepwell polypropylene plate in triplicate. Ten L of the 50 M test compound was added to the microsomes and the mixture was pre-warmed for 10 minutes. Reactions were initiated by addition of pre-warmed NADPH solution. The final reaction volume was 0.5 mL and contained 0.5 mg/mL human liver microsomes, 1 M test compound, and 2 mM NADPH in 0.1 M potassium phosphate buffer, pH 7.4, and 3 mM $MgCl_2$. The reaction mixtures were incubated at 37° C., and 50 L aliquots were removed at 0, 5, 10, 20, and 30 minutes and added to shallow-well 96-well plates which contained 50 L of ice-cold ACN with internal standard to stop the reactions. The plates were stored at 4° C. for 20 minutes after which 100 L of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer.

The in vitro $t_{1/2}$s for test compounds were calculated from the slopes of the linear regression of % parent remaining (ln) vs incubation time relationship:
in vitro $t_{1/2}$=0.693/k, where k=−[slope of linear regression of % parent remaining(ln) vs incubation time]. Data analysis was performed using Microsoft Excel Software. The results of this experiment are shown in Table 3.

TABLE 3

In vitro Half-lives of Compounds in Human Liver Microsomes

| Compound | $t_{1/2}$ (min) | SD |
|---|---|---|
| Cilostazol | 46.8 | 6.36 |
| 107 | 35.7 | 3.44 |
| 101 | 45.2 | 9.48 |
| 106 | 79.5 | 0.74 |
| 100 | 41.7 | 2.48 |
| 110 | 74.5 | 4.92 |

Under the assay conditions, the half-lives of Compounds 106 and 110 were each between 60 and 70% longer than that of cilostazol.

The experiment was repeated using additional compounds of the invention and also the undeuterated cilostazol metabolite dehydrocilostazol:

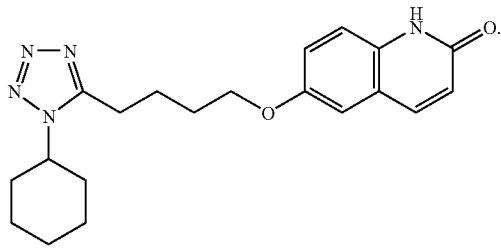 [SMILES: O=c1ccc2cc(OCCCCc3nnnn3C3CCCCC3)ccc2[nH]1]

The experiment was also repeated with Compound 100, which showed no stabilization in the previous experiment despite containing deuterium at each Y, as well as in Q (Q is —CD$_2$CD$_2$- in Compound 100). The results are shown in Table 4.

TABLE 4

In vitro Half-lives of Compounds in Human Liver Microsomes

| Compound | $t_{1/2}$ (min) | SD |
|---|---|---|
| Cilostazol | 61.8 | 2.7 |
| 106 | 86.9 | 6.5 |
| 100 | 98.6 | 13.8 |
| 112 | 79.5 | 12.0 |
| Dehydrocilostazol | 78.4 | 3.5 |
| 110 | Stable* | |
| 113 | 89.6 | 13.2 |

*less than 10% metabolism observed after 30 minutes incubation

These data confirmed that Compounds 106 and 110 were stabilized in comparison to their undeuterated counterparts— cilostazol and dehydrocilostazol, respectively. The data here showed that Compound 100 was stabilized as compared to cilostazol.

While this invention has been particularly shown and described with references to example embodiments thereof, it will be understood by those skilled in the art that various changes in form and details may be made therein without departing from the scope of the invention encompassed by the appended claims.

What is claimed is:
1. A compound of Formula II:

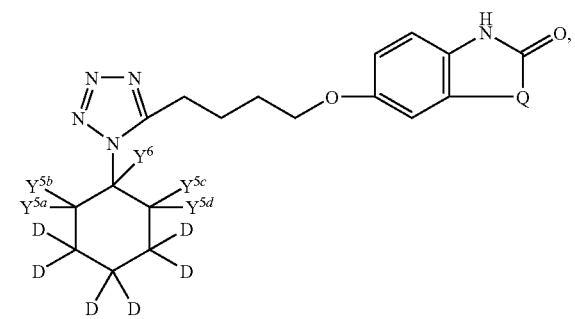

wherein:
each Y is independently selected from hydrogen and deuterium; and
Q is —CH$_2$CH$_2$—, —CD$_2$CD$_2$-, —CH$_2$CD$_2$-, CD$_2$CH$_2$—, —CD=CD—, or —CH=CH—, wherein any atom not designated as deuterium is present at its natural isotopic abundance.

2. The compound of claim 1, wherein each $Y^5$ is the same.
3. The compound of claim 1, wherein Q is —CH$_2$CH$_2$—or —CH=CH—.
4. The compound of claim 1, selected from Compound 106

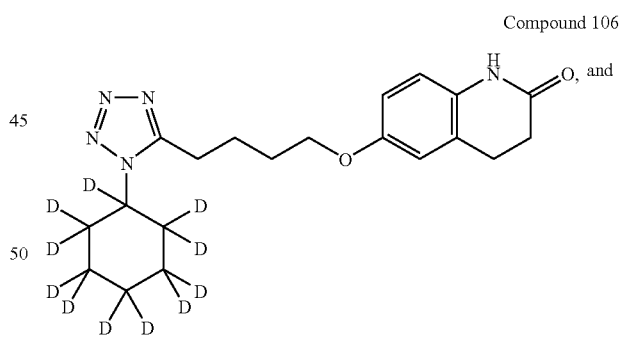

Compound 110

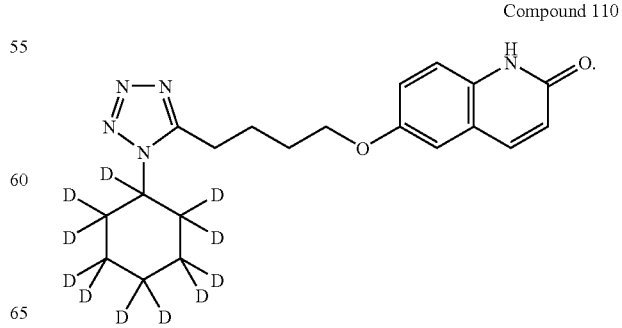

5. A pharmaceutical composition comprising a compound of claim 1 and a pharmaceutically acceptable carrier.

6. The composition of claim 5, further comprising a second therapeutic agent useful in treating a patient suffering from or susceptible to arterial occlusive disease, intermittent claudication or stroke.

7. The composition of claim 6, wherein the second therapeutic agent is selected from aspirin, clopidogrel and probucol.

8. A method of treating a disease selected from chronic arterial occlusive disease, intermittent claudication, or stroke, in a patient in need thereof, comprising the steps of administering to the patient the pharmaceutical composition of claim 5.

\* \* \* \* \*